United States Patent [19]

Kawabuchi et al.

[11] Patent Number: 4,895,158
[45] Date of Patent: Jan. 23, 1990

[54] ULTRASONIC PROBE

[75] Inventors: Masami Kawabuchi, Yokohama; Fumio Muramatsu, Atsugi, both of Japan

[73] Assignee: Matsushita Electric Industrial Co., Ltd., Osaka, Japan

[21] Appl. No.: 300,216

[22] Filed: Jan. 24, 1989

Related U.S. Application Data

[63] Continuation of Ser. No. 70,256, Jul. 6, 1987, abandoned.

[30] Foreign Application Priority Data

Jul. 7, 1986 [JP] Japan .......................... 61-104044[U]
Jul. 15, 1986 [JP] Japan .......................... 61-108465[U]
Jul. 15, 1986 [JP] Japan .............................. 61-165839

[51] Int. Cl.$^4$ .............................................. A61B 8/12
[52] U.S. Cl. .................................................. 128/662.06
[58] Field of Search ................ 73/618, 620, 621, 629, 73/633; 128/662.06, 4, 6, 661; 367/104

[56] References Cited

U.S. PATENT DOCUMENTS

| | | | |
|---|---|---|---|
| 2,764,148 | 9/1956 | Sheldon | 128/4 |
| 3,454,923 | 7/1969 | Currie | 367/173 |
| 3,817,089 | 6/1974 | Eggleton et al. | 73/623 |
| 4,271,706 | 6/1981 | Ledley | 73/620 |
| 4,282,879 | 8/1981 | Kunii et al. | 128/660 |
| 4,375,818 | 3/1983 | Suwaki et al. | 128/4 |
| 4,399,703 | 8/1983 | Matzuk | 128/660 |
| 4,417,583 | 11/1983 | Bechai et al. | 128/4 |
| 4,558,706 | 12/1985 | Nakada et al. | 128/660 |
| 4,674,515 | 6/1987 | Andou et al. | 128/660 |
| 4,756,313 | 7/1988 | Terwilliger | 128/4 |
| 4,785,819 | 11/1988 | Pearce | 73/634 |

FOREIGN PATENT DOCUMENTS

| | | |
|---|---|---|
| 0039045 | 11/1981 | European Pat. Off. . |
| 0065275 | 11/1982 | European Pat. Off. . |
| 53-83370 | 7/1978 | Japan . |
| 59-131339 | 7/1984 | Japan . |

OTHER PUBLICATIONS

Millman, Jacob, "Microelectronics-Digital and Analog Circuits and Systems" McGraw-Hill Book Co. (1979) p. 19.

Primary Examiner—John Chapman
Assistant Examiner—Lawrence Fess
Attorney, Agent, or Firm—Lowe, Price, LeBlanc, Becker & Shur

[57] ABSTRACT

An ultrasonic transducer element is supported by a member. The transducer element and the supporting member are disposed within a casing filled with ultrasonic wave propagation medium. At least part of the casing forms an ultrasonic wave transmission window. In a first case, the supporting member is rotatable about a first axis and about a second axis, and the position of the supporting member is detected. In a second case, the casing has a first portion accommodating the transducer element and the supporting member and a second portion extending in rear of the first portion and being narrower than the first portion, and the transducer element is allowed to emit and receive ultrasonic wave to and from a region extending in front of the casing with resepct to a direction of insertion of the casing into a body to be examined. In a third case, a sensor detects at least one condition related to opreation of a mechanism driving the supporting member.

11 Claims, 6 Drawing Sheets

ULTRASONIC PROBE

This application is a continuation of application Ser. No. 070,256, filed July 6, 1987, now abandoned.

BACKGROUND OF THE INVENTION

1. Field of the Invention

This invention relates to an ultrasonic probe usable in ultrasonic systems such as medical ultrasonic diagnostic systems.

2. Description of the Prior Art

Some medical ultrasonic diagnostic systems produce sectional images of bodies. These systems generally have ultrasonic probes which scan beams of ultrasonic wave pulses to produce sectional images of bodies. There are ultrasonic probes of the mechanically scanning type. Some ultrasonic probes are inserted into and used in coeloms of a body to produce sectional images of internal organs. As will be described hereinafter, conventional ultrasonic probes have various problems, particularly of this type.

SUMMARY OF THE INVENTION

It is a first object of this invention to provide a small ultrasonic probe for insertion into coeloms of a body to produce sectional images of internal organs.

It is a second object of this invention to provide an ultrasonic probe which generates an acceptably low level of vibration.

It is a third object of this invention to provide an ultrasonic probe which can produce sectional images over a wide angular range.

It is a fourth object of this invention to provide an easily handleable ultrasonic probe that is easy to handle.

It is a fifth object of this invention to provide an ultrasonic probe which produce sectional images in a region where sectional images are generally unavailable heretofore.

It is a sixth object of this invention to provide an ultrasonic probe which inflicts only an acceptably low level of pain on a patient during insertion of the probe into the body of the patient.

It is a seventh object of this invention to provide an ultrasonic probe which can absorb load variations.

It is an eighth object of this invention to provide an ultrasonic probe which is easy and inexpensive to manufacture.

Other related objects and advantages of the present invention will become apparent to persons skilled in the art upon their developing an understanding of the following description thereof.

In an ultrasonic probe according to a first aspect of this invention, an ultrasonic transducer element is supported by a rotatable support member. An accommodation member accommodates the support member and is filled with an ultrasonic wave propagation medium. A rigidly formed shaft-shaped portion, comprising an outer tube comprising synthetic resin and an outer tube comprising synthetic resin and an inner tube made of metal, extends rearwardly of the accommodation portion and accommodates a drive shaft perpendicular to a rotation axis of the support member, the shaft-shaped portion being thinner than the accommodating portion and also being filled with the ultrasonic wave propagation medium. The ultrasonic oscillator is located offset with respect to the drive shaft axis, whereby ultrasonic waves are transmitted and received via the ultrasonic oscillator, and a radially-shaped ultrasonic wave sectional image is obtained in a sectional plane parallel to a sectional plane including the drive shaft.

In another aspect of the invention the probe further comprises a drive section driving both the support member and the drive shaft, with a sealing member provided in a drive accommodation portion.

In other aspects of the invention, means including one or, optionally, two motors are provided to drive the support member about corresponding first and/or second axes.

DESCRIPTION OF THE PREFERRED EMBODIMENTS

Prior to the description of embodiments of this invention, known ultrasonic probes will be described hereinafter for a better understanding of this invention.

Figure 1:
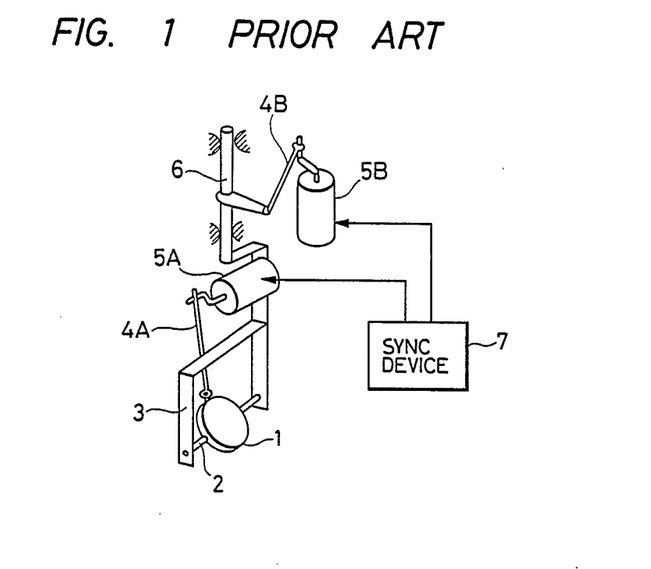
FIG. 1 is a diagram of a known ultrasonic probe.

FIG. 1 shows a known ultrasonic probe of the mechanically scanning type disclosed in Japanese published unexamined patent application 53-83370. In the known ultrasonic probe of FIG. 1, an ultrasonic transucer element or head 1 is rotatably supported on a frame 3 via a shaft 2. The transducer element 1 is connected via a link 4A to a power source 5A, such as an electric motor, a pneumatic actuator, or a hydraulic actuator. The power source 5A can rotate the transducer element 1 about the shaft 2 in a limited angular range. A synchronizing device 7 controls operation of the power source 5A. The rotation of the transducer element 1 by the power source 5A allows a sector scan of a beam of ultrasonic wave pulses emitted from the transducer element 1. This scan produces a sectoral section image of a body.

A direction shaft 6 carrying the frame 3 is connected via a link 4B to a power source 5B, such as an electric motor, a pneumatic actuator, or a hydraulic actuator. The power source 5B can rotate the frame 3 about the direction shaft 6. Accordingly, at varying directions or angular positions of the frame 3, sectoral section images of the body are available. The synchronizing device 7 controls operation of the power source 5B.

In the known ultrasonic probe of FIG. 1, the transducer element drive mechanism composed of the link 4A and the power source 5A considerably limits the angle of the sector scan of the beam of ultrasonic wave pulses. The links 4A and 4B cause the probe to be large. Since the transducer element 1 and the frame 3 are subjected to reciprocating rotational movements in limited angular ranges, significant mechanical vibrations tend to be generated.

Figure 2:
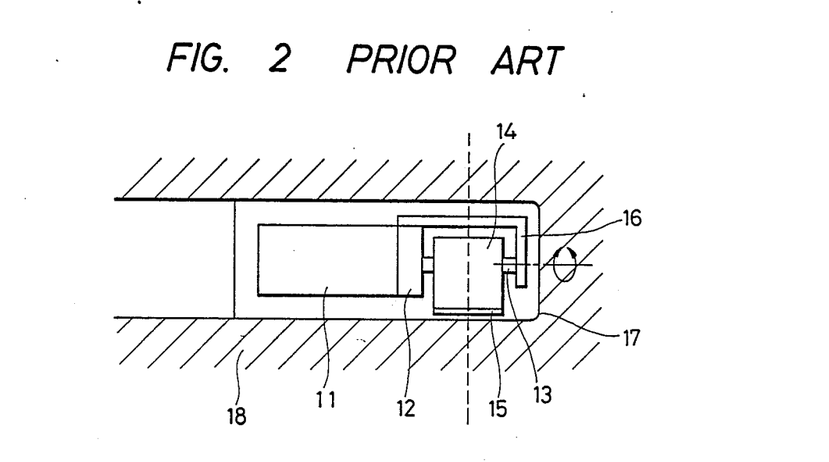
FIG. 2 is a sectional view of an organ and another known ultrasonic probe.

Japanese published unexamined patent application 59-131339 discloses an ultrasonic probe designed to be used in coeloms of a body to produce sectional images of internal organs. FIG. 2 shows such a known ultrasonic probe. In the known ultrasonic probe of FIG. 2, a pulse motor 11 is connected to a damper 14 via a micro gear head 12 and a shaft 13. The damper 14 carries an ultrasonic transducer element or head 15. The shaft 13 is supported by a plate 16. The devices 11-16 are accommodated in a casing 17. As shown in FIG. 2, the ultrasonic probe is inserted into an organ 18 of a body.

The pulse motor 11 serves to rotate the damper 14 and the transducer element 15 about the shaft 13. The micro gear head 12 reduces the rotational speed of the transducer element 15 in comparison with the rotational speed of the pulse motor 11. The rotation of the transducer element 15 by the pulse motor 11 allows a sector scan of a beam of ultrasonic wave pulses emitted from the transducer element 15. This scan of the beam of ultrasonic wave pulses produces a sectoral section image of the organ 18.

In the known ultrasonic probe of FIG. 2, since the transducer element 15 is rotatable only about the shaft 13, a section of the organ 18 which can be imaged extends along a plane (denoted by the broken line in FIG. 2) perpendicular to the shaft 13. Accordingly, it is generally difficult to take a sectional image of a portion of the organ 18 extending at and around an assumed extension of the shaft 13. Specifically, it is difficult to take a sectional image of a portion of the organ 18 extending in front of the casing 17 with respect to a direction of the insertion of the probe into the organ 18. In addition, since the casing 17 has a large outside diameter, a patient tends to suffer pain during the insertion and use of the probe.

In the known ultrasonic probes of FIGS. 1 and 2, it is generally difficult to limit variations in loads on the power sources 5A and 5B, and the pulse motor 11 within acceptably small ranges. Since the speeds of the transducer elements 1 and 15 fluctuate with variations in loads on the power devices 5A, 5B, and 11, available sectional images are degraded by these load variations. Such power device load variations are generally caused by dimensional errors of parts of the drive arrangements between the power devices and the transducer elements, and caused by temperature variations. Accordingly, in the known ultrasonic probes of FIGS. 1 and 2, the useful yield from a scan tends to be low.

Figure 3:
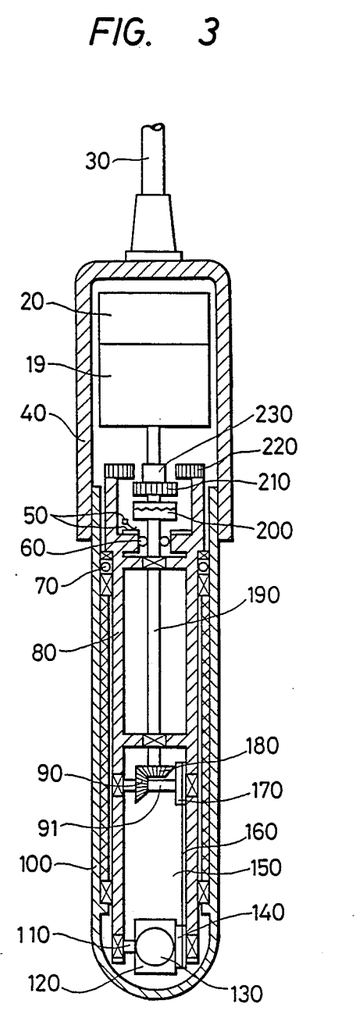
FIG. 3 is a sectional view of an ultrasonic probe according to a first embodiment of this invention.

FIG. 3 shows an ultrasonic probe according to a first embodiment of this invention. In the ultrasonic probe of FIG. 3, a motor 19 and an encoder 20 are disposed within a cylindrical casing 40. A cable 30 containing electric leads extends into the casing 40 and is electrically connected to the motor 19 and the encoder 20. The cable 30 is also electrically connected to a main portion of a medical ultrasonic diagnostic system (not shown). Various signals are transmitted between the main portion of the diagnostic system and the motor 19, and between the main portion of the diagnostic system and the encoder 20 via the cable 30. A chassis 80 is disposed within a housing or container 100 fixed to the casing 40. An ultrasonic transducer element or head 130 is attached to an outer surface of a support 120 which is rotatably connected to the chassis 80 via a shaft 110. The transducer element 130 is preferably provided with an acoustic matching layer and an acoustic lens in a known manner.

The distal forwardmost portion of the probe, i.e., the end housing the transducer element 130, as best seen in FIG. 3, is shaped to be smoothly rounded to facilitate easy insertion into the coelom without causing undue distress to the person being examined. The outer surface of the probe is made smoothly contiguous and sized to be as small as possible in the context of its intended use.

A signal transmission device 50 preferably composed of a slip ring is mounted on the chassis 80. A rotary transformer (not shown) is disposed within the support 120. The transducer element 130 is electrically connected to the cable 30 via the signal transmission device 50, the rotary transformer, and leads (not shown). It should be noted that the rotary transformer may be replaced by a slip ring.

The container 100 is filled with liquid ultrasonic wave propagation medium. An O-ring 60 provided between the chassis 80 and a shaft 190 prevents leakage of the ultrasonic wave propagation liquid. An O-ring 70 provided between the chassis 80 and the container 100 also prevents leakage of the ultrasonic wave propagation liquid. The container 100 is preferably made of a material permeable to ultrasonic waves so that the container 100 forms an ultrasonic wave transmission window. It should be noted that only a frontal portion of the container 100, i.e., adjacent the transducer element 130, needs to be designed to form an ultrasonic wave transmission window.

The motor 19 has a rotatable output shaft coaxial with the shaft 190. A clutch 200 provided between the motor shaft and the shaft 190 selectively connects and disconnects the shaft 190 to and from the motor shaft. The shaft 190 extends along a central axis of the chassis 80. A bevel gear 90 is fixedly mounted on a shaft 91 rotatably supported by the chassis 80. The shaft 91 extends perpendicular to the shaft 190. The bevel gear 90 meshes with a bevel gear 180 fixedly mounted on the shaft 190. A pulley 170 fixedly mounted on the shaft 91 is coupled via an endless belt 160 to a pulley 140 fixedly mounted on the shaft 110. The shaft 110 extends parallel to the shaft 91 and perpendicular to the shaft 190. In cases where the clutch 200 connects the shaft 190 to the motor shaft, when the motor 19 is activated, a rotational force is transmitted from the motor 19 to the support 120 via the motor shaft, the clutch 200, the shaft 190, the bevel gears 90 and 180, the shaft 91, the pulley 170, the belt 160, the pulley 140, and the shaft 110 so that the support 120 and the transducer element 130 rotate about the shaft 110. This rotation of the support 120 and the transducer element 130 is denoted by the arrow A in FIG. 4.

A gear 210 fixedly carried on a slider 230 connected to the motor shaft. The connection between the slider 230 and the motor shaft preferably includes a key coupling which allows the slider 230 to rotate together with the motor shaft and allows the slider 230 to move axially relative to the motor shaft. Since the gear 210 is fixed to the slider 230, the gear 210 rotates together with the motor shaft but is axially movable relative to the motor shaft. A gear 220 is secured to the chassis 80. As the gear 210 is moved axially by the slider 230, the gear 210 comes into and out of mesh with the gear 220. The chassis 80 is rotatably supported on the container 100 via bearings. The chassis 80 can rotate about the motor shaft and the shaft 190. Since the transducer element 130 is connected to the chassis 80 via the support 120 and the shaft 110, the transducer element 130 rotates together with the chassis 80. In cases where the clutch 200 disconnects the motor shaft from the shaft 190, when the gear 210 is moved into mesh with the gear 220 and the motor 19 is activated, a rotational force is transmitted from the motor 19 to the chassis 80 so that the chassis 80 and the transducer element 130 rotate about the motor shaft and the shaft 190. This rotation of the transducer element 130 is denoted by the arrow B in FIG. 4.

The clutch 200 is preferably of the electromagnetic type. In this case, the clutch 200 is electrically connected to the cable 30 via electric leads so that the clutch 200 is controllable via an electric signal outputted from the main portion of the diagnostic system. It should be noted that the clutch 200 may be controllable via a mechanical device which can be handled outside the casing 40. The slider 230 is preferably driven by an electric actuator or a solenoid disposed within the casing 40. In this case, the actuator or the solenoid is electrically connected to the cable 30 via electric leads so that the slider 230 is controllable via an electric signal outputted from the main portion of the diagnostic system. It should be noted that the slider 230 may be controllable via a mechanical device which can be handled outside the casing 40.

The encoder 20 is associated with the motor shaft. The encoder 20 generates an electric signal or signals representing the angular position of the motor shaft and the rotational speed of the motor shaft. These signals are transmitted to the main portion of the diagnostic system via the cable 30. The encoder 20 is preferably of the optical type or the electromagnetic type generating electric pulses in accordance with the rotation of the motor shaft. Since the position of the transducer element 130 depends on the angular position of the motor shaft, the position of the transducer element 130 is detected via the signal representing the angular position of the motor shaft.

Figure 4:
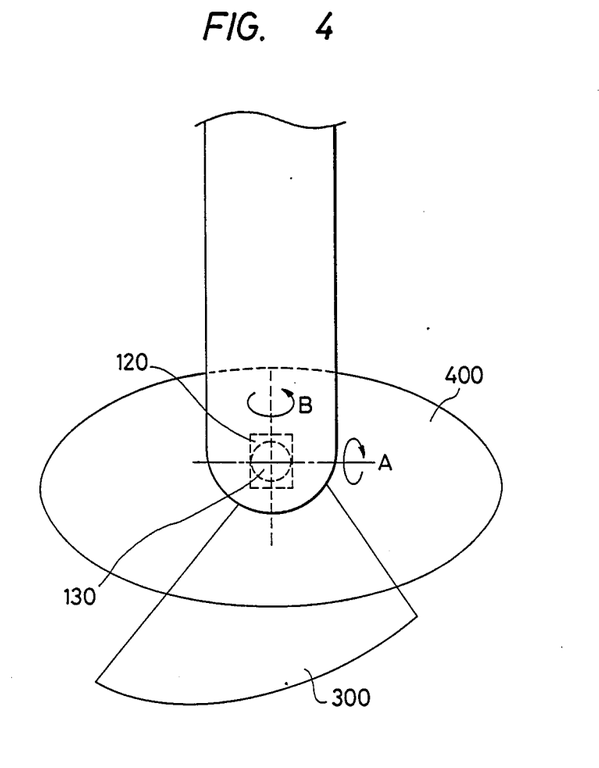
FIG. 4 is a diagram showing rotations of the support and the transducer element, and scanning planes in the ultrasonic probe of FIG. 3.

The ultrasonic probe of FIG. 3 operates as follows. The ultrasonic probe is generally inserted gently to a predetermined distance into a coelom of a body to be examined. First, the operation of the ultrasonic probe will be described with respect to cases where the slider 230 is moved to a position at which the gear 210 separates from the gear 220, and where the clutch 200 is controlled so that the shaft 190 is coupled to the motor shaft. Under these conditions, as the motor 19 is activated, the support 120 and the transducer element 130 rotate about the shaft 110 and in the direction denoted by the arrow A of FIG. 4. When the position of the transducer element 130 which is detected via the signal from the encoder 20 reaches a desired position or range, the main portion of the diagnostic system outputs an activation signal to the transducer element 130 via the cable 30, the signal transmission device 50, and the rotary transformer (not shown) within the support 120 so that the transducer element 130 is energized. Accordingly, the transducer element 130 emits a beam of ultrasonic wave pulses, which travels to the body via the ultrasonic wave propagation liquid 150 and the walls of the container 100. The body generally has uneven acoustic impedances which cause the ultrasonic wave pulses to be reflected. The reflected ultrasonic wave pulses return to the transducer element 130. The transducer element 130 converts the reflected and returned ultrasonic wave pulses into a corresponding electric signal, which is transmitted to the main portion of the diagnostic system via the rotary transformer within the support 120, the signal transnmission device 50, and the cable 30. The main portion of the diagnostic system processes this electric signal and thereby derives a display data signal corresponding to one scanning line in a known way. The data signal is indicated by a display such as a cathode-ray tube. The previously-mentioned operation to derive a display data signal corresponding one scanning line is periodically reiterated while the transducer element 130 is rotated through a desired angular range by the motor 19. In this way, the beam of ultrasonic wave pulses emitted from the transducer element 130 is scanned along a sector plane 300 as shown in FIG. 4, so that a corresponding sector sectional image of the body is obtained on the display. During this sector scanning process, the main portion of the diagnostic system monitors the position of the transducer element 130 via the signal from the encoder 20 and controls the position of the transducer element 130 in accordance with the monitored information via the signal to the motor 19 in conventional closed loop control. Furthermore, the main portion of the diagnostic system controls the speed of the motor 19 in accordance with the speed signal from the encoder 20 to regulate the rotational speed of the support 120 and the transducer element 130 at a constant value. The angle of the sector scan of the ultrasonic wave beam is, for example, 100°. The sector scan angle may be a full 360° or any other selected value. The support 120 and the transducer element 130 may be rotated in reciprocatory motion at a predetermined rate by a suitable actuator to thus produce a controlled scan of the ultrasonic wave beam.

Second, the operation of the ultrasonic probe will be described with respect to cases where the clutch 200 is controlled so that the shaft 190 is disconnected from the motor shaft, and where the slider 230 is moved to a position at which the gear 210 meshes with the gear 220. Under these condition, as the motor 19 is activated, the support 120 and the transducer element 130 rotate together with the chassis 80 about the motor shaft and the shaft 190 and in the direction denoted by the arrow B of FIG. 4. In these cases, the transducer element 130 is generally prelocated so as to face in the direction perpendicular to the motor shaft and the shaft 190. When the position of the transducer element 130 which is detected via the signal from the encoder 20 reaches a desired position or range, the main portion of the diagnostic system outputs an activation signal to the transducer element 130 via the cable 30, the signal transmission device 50, and the rotary transformer (not shown) within the support 120 so that the transducer element 130 is energized. Accordingly, the transducer element 130 emits a beam of ultrasonic wave pulses, which travel to the body via the ultrasonic wave propagation liquid 150 and the walls of the container 100. The body generally has uneven acoustic impedances which cause the ultrasonic wave pulses to be reflected. The reflected ultrasonic wave pulses return to the transducer element 130.

The transducer element 130 converts the reflected and returned ultrasonic wave pulses into a corresponding electric signal, which is transmitted to the main portion of the diagnostic system via the rotary transformer within the support 120, the signal transmission device 50, and the cable 30. The main portion of the diagnostic system processes this electric signal and thereby derives a display data signal corresponding to one scanning line in a known way. The data signal is indicated by the display.

In general, the previously-mentioned operation to derive a diaplay data signal corresponding to one scanning line is periodically reiterated while the transducer element 130 is rotated through an angle of 360° by the motor 19. In this way, the beam of ultrasonic wave pulses emitted from the transducer element 130 is scanned along a circular plane 400 as shown in FIG. 4, so that a corresponding circular sectional image of the body is obtained on the display. During this circular scanning process, the main portion of the diagnostic system monitors the position of the transducer element 130 via the signal from the encoder 20 and controls the position of the transducer element 130 in accordance with the monitored information via the signal to the motor 19 in conventional closed loop control. Furthermore, the main portion of the diagnostic system controls the speed of the motor 19 in accordance with the speed signal from the encorder 20 to regulate the rotational speed of the transducer element 130 at a constant value. It should be noted that the angle of the circular scan of the ultrasonic wave beam may be smaller than 360°.

As understood from the previous description, the ultrasonic probe of FIGS. 3 and 4 can produce sectional imgages of a body over a wide range. Furthermore, the ultrasonic probe of FIGS. 3 and 4 can easily produce a hemispherical image of a body when a sector scan and a circular scan are combined. In the ultrasonic probe of FIGS. 3 and 4, the power drive train is basically composed of the gears and the pulleys so that the level of generated vibrations is acceptably low.

Figure 5:
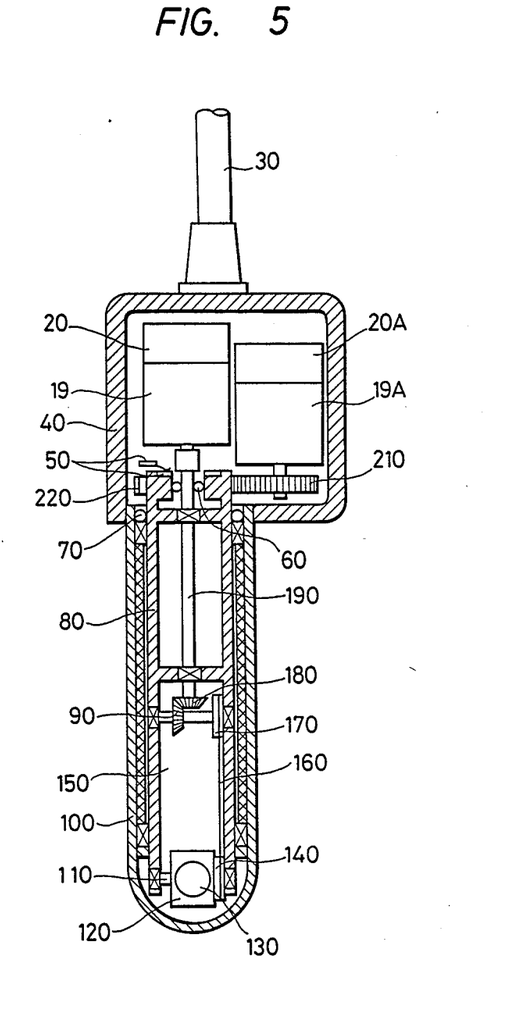
FIG. 5 is a sectional view of an ultrasonic probe according to a second embodiment of this invention.

FIG. 5 shows an ultrasonic probe according to a second embodiment of this invention. The second embodiment is similar to the embodiment of FIGS. 3 and 4 except for design changes described hereinafter.

In the ultrasonic probe of FIG. 5, the clutch 200 and the slide 230 (see FIG. 3) are omitted, and the shaft 190 is directly coupled to the output shaft of the motor 19. A second motor 19A and a second encoder 20A are disposed within the casing 40. A gear 210 fixedly mounted on an output shaft of the motor 19A meshes with a gear 220 fixed to the chassis 80. The second motor 19A is electrically connected to the cable 30 so that the second motor 19A can be controlled via an electric signal outputted from the main portion of the diagnostic system. The second encoder 20A is associated with the output shaft of the second motor 19A. The second encoder 20A generates an electric signal or signals representing the angular position of the output shaft of the second motor 19A and the rotational speed of the output shaft of the second motor 19A. The second encoder 20A is electrically connected to the cable 30 so that the electric signals are transmitted from the second encoder 20A to the main portion of the diagnostic system via the cable 30.

As the motor 19 is activated, the shaft 190 rotates so that the support 120 and the transducer element 130 rotate about the shaft 110. This rotation of the transducer element 130 allows a sector scan of the ultrasonic wave beam. As the second motor 19A is activated, the chassis 80 rotates so that the support 120 and the transducer element 130 rotate together with the chassis 80. This rotation of the transducer element 130 allows a circular scan of the ultrasonic wave beam. Since the position of the transducer element 130 depends on the angular position of the output shaft of the motor 19 and on the angular position of the output shaft of the second motor 19A so that the signals outputted from the encoders 20 and 20A represent the position of the transducer element 130. The main portion of the diagnostic system controls the motors 19 and 19A in accordance with the signals from the encorders 20 and 20A.

In the ultrasonic probe of FIG. 5, which at its distal or insertion end is shaped similarly to that described with reference to FIG. 3 earlier, the sector scanning mechanism and the circular scanning mechanism include separate motors and encoders respectively, so that a quick change between the sector scan and the circular scan is allowed.

It should be noted that in the motor power drive trains of the embodiments of FIGS. 3-5, the gears and the pulleys may be replaced by other suitable elements.

Figure 6:
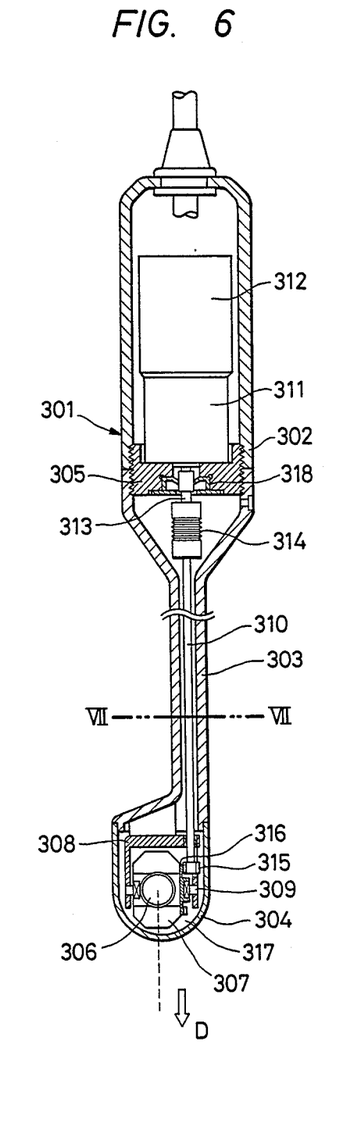
FIG. 6 is a sectional view of an ultrasonic probe according to a third embodiment of this invention.
Figure 7:
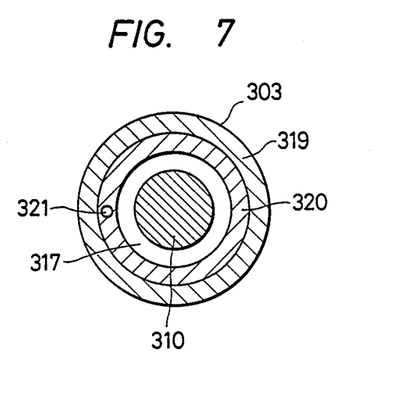
FIG. 7 is a sectional view of the ultrasonic probe taken along the line VII—VII in FIG. 6.

FIGS. 6 and 7 show an ultrasonic probe according to a third embodiment of this invention. The ultrasonic probe of FIGS. 6 and 7 includes a casing 301 having a drive member accommodating portion 302, a narrow elongated portion 303, and a transducer element accommodating portion 304. A first enlarged end of the elongated portion 303 is preferably connected to the drive member accommodating portion 302 by a connection member 305 fixed to the casing portions 302 and 303 via threads. A second enlarged end of the elongated portion 303 is connected to the transducer element accommodating portion 304.

A motor 311 and an encoder 312 are disposed within the casing portion 302. A drive shaft 310 is coaxially disposed within the casing portion 303. An ultrasonic transducer element 306 and a support 307 are disposed within the casing portion 304. At least the smoothly rounded forwardmost part of the transducer element accommodating portion 304 is formed with an acoustic window. The entire outside surface of the probe body, as best seen in FIG. 6, is formed to be smoothly contiguous to facilitate insertion into and manipulation of the transducer end within the body of the person being examined.

When the ultrasonic probe is used, it is inserted gently into a coelom of a body to a predetermined distance in the direction D (see FIG. 6) corresponding to a longitudinal axis of the casing 301.

The transducer element 306 is attached to an outer surface of the support 307. The support 307 is rotatably connected to a frame 308 via a shaft 309 extending perpendicular to the longitudinal axis of the casing 301 or the insertion direction B. The shaft 309 is also perpendicular to the drive shaft 310. The support 307 and the transducer element 306 can rotate about the shaft 309. Transducer 306 can be thus rotated through an angle of 360 degrees to generate a radially-shaped ultrasonic wave sectional image over an angular field larger than 180 degrees and up to 360 degrees. The frame 308 is supported by the casing portion 303. An end of the drive shaft 310 is rotatably supported by the frame 308. The other end of the drive shaft 310 is connected via a coupling 314 to an output shaft 313 of the motor 311 so that the drive shaft 310 can be rotated by the motor 311. The motor 311 is supported by the connection member 305.

A power transmission mechanism connects the drive shaft 310 and the support 317 so that the support 317 rotates about the shaft 309 as the drive shaft 310 rotates. The power transmission mechanism changes the direction of a transmitted rotational force such that the axis of rotation of the support 317 is perpendicular to the axis of rotation of the drive shaft 310. For example, the power transmission mechanism includes a combination of gears 315 and 316. The first gear 315 is fixedly mounted on the end of the drive shaft 310. The second gear 316 is attached to a side of the support 317. The gears 315 and 316 are in mesh. As the motor 311 is activated, the motor shaft 313 and the drive shaft 310 rotate together so that the support 307 and the transducer element 306 rotate together about the shaft 309.

The elongated portion 303 and the transducer element accommodating portion 304 are filled with ultrasonic wave propagation liquid 317 composed of deaerated water, butanediol, or others. A sealing member 318 provided between the connection member 305 and the motor shaft 313 prevents leakage of the ultrasonic wave propagation liquid 317. Such a location of the sealing member 318 ensures the narrow design of a major part of the elongated casing portion 303.

As shown in FIG. 7, the elongated casing portion 303 includes an outer tube 319 and an inner tube 320 extending coaxially. The outer tube 319 is made of insulating material such as synthetic resin to prevent electric leakage from the ultrasonic probe to an examined body. The outer tube 320 is made of metal to increase the strength of the casing 301.

The motor 311 is electrically connected via a cable (no reference character) to a main portion (not shown) of a medical ultrasonic diagnostic system so that the motor 311 is controlled via an electric signal outputted from the main portion of the diagnostic system. The encoder 312 is associated with the motor shaft 313. The encoder 312 generates an electric signal or signals representing the angular position of the motor shaft 313 and the rotational speed of the motor shaft 313. Since the position of the transducer element 306 depends on the angular position of the motor shaft 313, the electric signal outputted by the encorder 312 also represents the position of the transducer element 306. The encoder 312 is electrically connected via the cable to the main portion of the diagnostic system so that the signal or signals are transmitted from the encoder 312 to the main portion of the diagnostic system.

The transducer element 306 is electrically connected to the main portion of the diagnostic system so that electric signals are transmitted between the transducer element 306 and the main portion of the diagnostic system. The electrical connection between the transducer element 306 and the main portion of the diagnostic system includes the cable, and leads disposed in the casing 301 and extending between the transducer element 306 and the cable. As shown in FIG. 7, the inner casing tube 320 has an axial hole 321 through which these leads extend. The metal inner tube 320 is electrically grounded to reduce the ingress of foreign noises into signals travelling along the leads. It should be noted that the leads are electrically insulated from the metal inner tube 320 by a suitable insulating arrangement.

For example, the transducer element accommodating portion 304 has an outside diameter of about 20 mm and a length of about 30 mm, and the elongated portion 303 has an outside diameter of about 10 mm and a length of about 110 mm.

The ultrasonic probe of FIGS. 6 and 7 operates as follows. When the ultrasonic probe is used, it is inserted into a coelom of a body to be examined. The narrow design of the casing elongated portion 303 significantly reduces the pain that will be experienced by the patient during the insertion of the ultrasonic probe into his or her body. After the ultrasonic probe is inserted into the body, the motor 311 is activated so that the drive shaft 310 rotates together with the motor shaft 313 and the coupling 314. The rotational force is transmitted from the drive shaft 310 to the support 307 via the gears 315 and 316, thereby rotating the support 307 and the transducer element 306.

During the rotation of the transducer element 306, the transducer element 306 is activated so that a beam of ultrasonic wave pulses are emitted from the transducer element 306 into the examined body via the ultrasonic wave propagation liquid 317 and the acoustic window of the casing portion 304. Some of the emitted ultrasonic wave pulses are reflected by the examined body and return to the transducer element 306 via the acoustic window of the casing portion 304 and the ultrasonic wave propagation liquid 317. The transducer element 306 converts the reflected and returned ultrasonic wave pulses into a corresponding electric signal, which is transmitted to the main portion of the diagnostic system. The main portion of the diagnostic system processes this electric signal and thereby derives a display data signal corresponding to one scanning line in a known way. The data signal is indicated by a display such as a cathode-ray tube.

In general, the previously-mentioned operation to derive a display data signal corresponding one scanning line is periodically reiterated while the transducer element 306 is rotated through a desired angle by the motor 311. In this way, the beam of ultrasonic wave pulses emitted from the transducer element 306 on the forwardmost part of the probe is scanned along a sector plane extending frontward of the ultrasonic probe with respect to the insertion direction D, so that a corresponding sector sectional image of the portion of the body extending frontward of the ultrasonic probe is obtained on the display. During this sector scanning process, the main portion of the diagnostic system monitors the position of the transducer element 306 via the signal from the encoder 312 and controls the position of the transducer element 306 in accordance with the monitored information via the signal to the motor 311 in conventional closed loop control. Furthermore, the main portion of the diagnostic system controls the speed of the motor 311 in accordance with the speed signal from the encoder 312 to regulate the speed of rotation of the support 307 and the transducer element 306 at a constant value.

Two or more ultrasonic transducer elements 306 may be arranged on the support 307. In this case, the support may be rotated in one direction only. In the case where a single transducer element 306 is provided, the support 307 may be rotated through a given angular range in reciprocatory motion. The mechanical scanning arrangement may be replaced by an electronic scanning system in which the transducer element is of the linear array type, the faced array type, or the convex array type.

Figure 8:
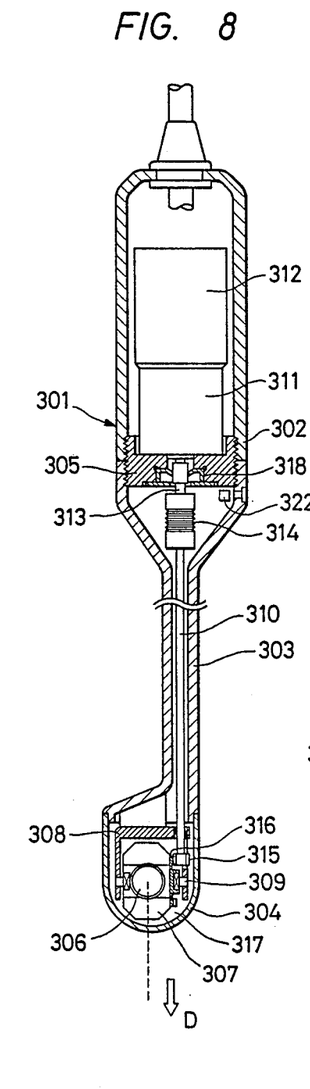
FIG. 8 is a sectional view of an ultrasonic probe according to a fourth embodiment of this invention.
Figure 9:
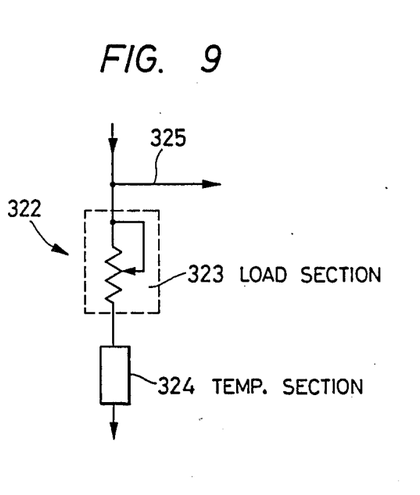
FIG. 9 is a diagram of an internal design of the condition sensor unit of FIG. 8.

FIGS. 8 and 9 show an ultrasonic probe according to a fourth embodiment of this invention. The fourth embodiment is similar to the embodiment of FIGS. 6 and 7 except for design changes described hereinafter.

In the embodiment of FIGS. 8 and 9, a condition sensor unit 322 disposed within the casing portion 302 generates an electric signal representing conditions related to operation of the motor 311. The condition sensor unit 322 is electrically connected to the main portion of the diagnostic system via the cable so that the electric signal is transmitted from the condition sensor unit 322 to the main portion of the diagnostic system.

As shown in FIG. 9, the condition sensor unit 322 includes a load section 323 and a temperature section 324 connected in series with a constant current supply (not shown). An electric line 325 connected between the condition sensor unit 322 and the main portion of the diagnostic system transmits the electric signal from the condition sensor unit 322 to the main portion of the diagnostic system.

The load section 323 includes a variable resistor. The resistance of this variable resistor is predetermined as follows. After the assembly of the ultrasonic probe is completed, the motor 311 is driven by a varying drive direct current at a given temperature, and the value of the drive current at which the speed of the motor 311 equals a reference speed is detected. The resistance of the variable resistor is preset so as to correspond to this detected value of the drive current. Accordingly, the electric signal outputted via the electric line 325 represents this detected value of the drive current.

The temperature section 324 includes a temperature responsive device or other known devices such as a diode and a thermistor (not shown in FIG. 9 because of their relatively small size). The resistance of the temperature section 324 varies with the temperature within the casing portion 302. Accordingly, the electric signal outputted via the electric line 325 represents the temperature within the casing portion 302.

The main portion of the diagnostic system includes a phase-locked loop (PLL) circuit which basically serves to control the drive current of the motor 311 in accordance with the signal from the encoder 312 so as to regulate the rotational speed of the support 307 and the transducer element 306 at a constant value. The signal outputted from the condition sensor unit 322 is used in the constant rotational speed control of the support 307 and the transducer element 306 to increase the reliability and the response characteristic of the control. Specifically, the signal outputted from the condition sensor unit 322 is used to compensate variations in the load on the motor 311 caused by dimensional errors of the parts and temperature changes. Accordingly, the PLL circuit can operate effectively and the yield during manufacture can be improved.

It should be noted that modification may be made in the embodiment of FIGS. 8 and 9. For example, the condition sensor unit 322 may be located at other places. The condition sensor unit 322 may be embedded in the walls of the casing portion 302. One of the load section 323 and the temperature section 324 may be omitted from the condition sensor unit 322.

The above-discussed description is set forth to illustrate various embodiments of the invention and is not intended to limit the scope of the present invention. Additional embodiments and advantages within the scope of the claimed invention will be apparent to one of ordinary skill in the art.

What is claimed is:

1. An elongate ultrasonic probe shaped and sized for insertion into coeloms of a body, comprising:
   an ultrasonic transducer element;
   a rotatable member supporting the transducer element;
   a casing accommodating the transducer element and the supporting member and filled with ultrasonic wave propagation medium, wherein at least the forwardmost part of the casing is smoothly rounded and smoothly contiguous with the elongate portion of the casing to reduce discomfort to the person receiving the probe, this forwardmost part forming an ultrasonic wave transmission window;
   means for controllably rotating the supporting member about a first axis and also about a second axis orthogonal to the first axis; and
   means for detecting the positions of the supporting member with respect to both said first and second axes.

2. The ultrasonic probe of claim 1, wherein:
   the rotating means comprises a motor, and means for allowing the motor to controllably rotate the supporting member selectively about the first axis and about the second axis.

3. The ultrasonic probe of claim 1, wherein:
   the rotating means comprises a first motor, means for allowing the first motor to controllably rotate the supporting member about the first axis, a second motor, and means for allowing the second motor to controllably rotate the supporting member about the second axis.

4. An elongate ultrasonic probe with a smooth contiguous outer surface shaped and sized for easy insertion into coeloms of a body, comprising:
   an ultrasonic transducer element;
   a rotatable member supporting the transducer element;
   a casing having a first portion and a second portion, the first casing portion accommodating the transducer element and the supporting member and filled with ultrasonic wave propagation medium, wherein at least the forwardmost part of the first casing portion is smoothly rounded to reduce discomfort to the person receiving the probe and also forms an ultrasonic wave transmission window, the second casing portion extending rearwardly of the first casing portion and being of smaller cross-section than the first casing portion; and
   means for allowing the transducer element to emit and receive an ultrasonic wave to and from a region extending in front of the casing with respect to a direction of insertion of the casing into the body of the person to be examined with the probe, wherein
   said accommodation portion has an outside diameter of about 20 mm and a length of about 30 mm, and the second casing portion has an outside diameter of about 10 mm and a length of about 100 mm and all outside surfaces thereof are smoothly contiguous and rounded to be free of any sharp edges or corners at least over said lengths.

5. The ultrasonic probe of claim 4, wherein:
   the second casing portion comprises an outer tube made of a synthetic resin that is electrically non-conductive and a rigid inner tube made of metal, the inner tube having an axial hole for accommodating electric leads connected to the transducer element.

6. The ultrasonic probe of claim 4, further comprising:
   means for detecting at least one condition related to operation of the driving means.

7. The ultrasonic probe of claim 6, wherein:
   the detecting means comprises means for sensing a load on the driving means, and means for sensing a temperature of the driving means during operation of the probe.

8. The ultrasonic probe of claim 5, wherein:
the inner metal tube is electrically grounded.

9. The ultrasonic probe of claim 4, wherein:
said accommodation portion has an outside diameter of about 20 mm and a length of about 30 mm; and
the second casing portion has an outside diameter of about 10 mm and a length of about 100 mm and all outside surfaces thereof are smoothly contiguous and rounded to be free of any sharp edges or corners at least over said lengths.

10. An ultrasonic probe for use within a coelom of a patient's body, comprising:
a movable support member provided with at least one ultrasonic oscillator;
an ultrasonic oscillator accommodation portion shaped to be smoothly rounded at the forwardmost end of the probe body and contiguous therewith for accommodating the support member and filled with ultrasonic wave propagation medium, wherein at least the rounded part of the accommodation portion has an ultrasonic wave transmission window;
a rigidly formed shaft-shaped portion, comprising an outer tube comprising synthetic resin and an inner tube made of metal, extending rearwardly of the accommodation portion and accommodating a drive shaft perpendicular to a rotation axis of the support member, the shaft-shaped portion being thinner than the accommodating portion and being filled with ultrasonic wave propagation medium, the ultrasonic oscillator being located at an offset portion with respect to the drive shaft to be rotatable with said movable support member thereat, whereby ultrasonic waves are transmitted and received via the ultrasonic oscillator over an angular field greater than 180 degrees, and a radially-shaped ultrasonic wave sectional image is obtained in a sectional plane parallel to a sectional plane including the drive shaft and frontwardly thereof.

11. The ultrasonic probe of claim 10, further comprising:
a drive section rotatably driving the support member via the drive shaft, a drive section accommodation portion accommodating the drive section, and a sealing member provided in the drive section accommodation portion to provide sealing of the ultrasonic wave propagation medium.

* * * * *